(12) United States Patent
Keimes et al.

(10) Patent No.: US 9,498,504 B2
(45) Date of Patent: Nov. 22, 2016

(54) **PROCESS FOR THE PREPARATION OF A PHARMACEUTICALLY EFFECTIVE EXTRACT FROM *ARTHROSPIRA* SP.**

(75) Inventors: Jorg Keimes, Reinbek (DE); Patrick Gunther, Aumuhle (DE)

(73) Assignee: Ocean Research & Development GmbH, Reinbek (DE)

( * ) Notice: Subject to any disclaimer, the term of this patent is extended or adjusted under 35 U.S.C. 154(b) by 402 days.

(21) Appl. No.: 14/124,108

(22) PCT Filed: May 4, 2012

(86) PCT No.: PCT/DE2012/000455
§ 371 (c)(1),
(2), (4) Date: Dec. 5, 2013

(87) PCT Pub. No.: WO2013/004205
PCT Pub. Date: Jan. 10, 2013

(65) Prior Publication Data
US 2014/0127336 A1    May 8, 2014

(30) Foreign Application Priority Data
Jul. 6, 2011  (DE) .................. 10 2011 107 307

(51) Int. Cl.
*A61K 35/748*   (2015.01)
(52) U.S. Cl.
CPC ......... *A61K 35/748* (2013.01); *A61K 2236/15* (2013.01); *A61K 2236/33* (2013.01)
(58) Field of Classification Search
CPC ................................................. A61K 35/748
USPC ....................................................... 424/780
See application file for complete search history.

(56) References Cited

U.S. PATENT DOCUMENTS

| | | | | |
|---|---|---|---|---|
| 4,756,319 A | * | 7/1988 | Takanashi ................ | A24D 3/14 131/334 |
| 2005/0281839 A1 | * | 12/2005 | Belay ................... | A61K 31/315 424/195.17 |
| 2007/0082008 A1 | * | 4/2007 | Harel .................... | A23K 1/007 424/195.16 |
| 2009/0123429 A1 | * | 5/2009 | Duncan ................. | A01N 63/00 424/93.4 |
| 2010/0272940 A1 | * | 10/2010 | Shi ...................... | B29C 45/0001 428/36.92 |

FOREIGN PATENT DOCUMENTS

| | | | |
|---|---|---|---|
| CN | 1288681 A | * | 3/2001 |
| CN | 101283756 A | * | 10/2008 |
| WO | WO 2006/047830 | | 5/2006 |
| WO | WO 2010/125490 | | 11/2010 |

OTHER PUBLICATIONS

Ozdemir et al., "*Antibacterial Activity of Volatile Component and Various Extracts of Spirulina platensis*", Phytotherapy Research, No. 18, pp. 754-757, 2004.
Chirasuwan et al., "*Anti HSV-1 Activity of Sulphoquinovosyl Diacylglycerol Isolated from Spirulina platensis*", ScienceAsia, No. 35, pp. 137-141, 2009.

* cited by examiner

*Primary Examiner* — Chris R Tate
(74) *Attorney, Agent, or Firm* — Diederiks & Whitelaw, PLC

(57) ABSTRACT

A process for the preparation of a pharmaceutically effective extract from the cyanobacterium *Arthrospira* sp. having the following steps: extrusion of a powder containing *Arthrospira* sp. with the addition of water; extraction of the extrudate with an organic solvent; and provision of the extract as a pharmaceutically effective composition.

17 Claims, No Drawings

PROCESS FOR THE PREPARATION OF A PHARMACEUTICALLY EFFECTIVE EXTRACT FROM *ARTHROSPIRA* SP.

CROSS-REFERENCE TO RELATED APPLICATIONS

This application represents a National Stage application of PCT/DE2012/000455 entitled "Process for the Preparation of a Pharmaceutically Effective Extract from *Arthrospira* Spec." filed May 4, 2012, pending.

BACKGROUND OF THE INVENTION

The invention relates to a process for the preparation of a pharmaceutically effective extract from the cyanobacterium *Arthrospira* sp.

It has been known for an extended period of time that aquatic organisms have developed in multiplicity of molecular defense mechanisms against microbial, in particular bacterial and fungal attack. As molecular-biological processes continue to advance, these molecules have recently also become the focus of research for medical applications for animal diseases.

Different algae and cyanobacteria should in particular be mentioned here that are not only the subject of pure research into molecular defense mechanisms, but inter alia also represent an important economic factor as food supplements in particular on account of their production of pharmaceutically effective substances.

About the cyanobacterium *Arthrospira* sp. for example it is known that it produces anti-microbially effective substances under physiological stress, it being possible for the substances to be concentrated using suitable extraction steps and to use them for treating various diseases. Such a process is for example known from WO 2006/047830 A1.

However it is difficult to determine or to adjust the stress conditions under which the organisms that are used to produce certain substances produce a maximum of the desired substances, so that often only little of the desired substances is produced or the conditions are set too harsh, the organisms dying as a result.

It is therefore the object of the invention to provide a process for the preparation of a pharmaceutically effective extract from *Arthrospira* sp. using which the naturally occurring content of pharmaceutically effective substances can be extracted from the organisms to a high degree. In the process, the extract that has been obtained is to exhibit good anti-microbial, in particular bactericide and fungicide action.

SUMMARY OF THE INVENTION

The basic idea of the invention is to use for the cell disruption a conventional extruder that is present anyway in the *Arthrospira* processing industry for the production of products in tablet form.

In particular it is provided to extrude a powder that can be obtained off the shelf as *spirulina* powder from dried *Arthrospira* individuals, in particular the cyanobacterium *Arthrospira maxima, Arthrospira fusiformis* or *Arthrospira platensis*, by adding water at a temperature in each case between 130° C. and 160° C., inclusive, and a pressure between in each case 8 MPa and 13 MPa, inclusive (corresponds to 80 to 130 bar), so that temperatures of at most 160° C. occur at the die head of the extruder only for a short time. The selection of an extruder that is suitable for the inventive process therefore depends on the possibility to use water as the solvent and also on the parameters mentioned above that essentially should not be exceeded, but also not undercut.

In a step that follows, the *Arthrospira* constituents are extracted using an organic solvent, preferably ethyl acetate. Particularly preferably, 10 mL of ethyl acetate are used here per 1 g of extrudate, the extraction extremely preferably taking place over a period of time of 24 hours at 28° C.

So that finally a product can be achieved that is ready to be marketed, the solvent used during the extraction can be removed, for example evaporated off in a rotary evaporator. Particularly preferably, the extract remaining after the solvent has been removed is filtered for decolouring and/or for removing the odour of the extract, e.g. using activated carbon, so that finally an aqueous extract is obtained that can be used for therapeutic or prophylactic purposes in human or veterinary-medical areas. On top of this, it is also conceivable that the extract can be used in the cosmetic field.

Using an exemplary embodiment of particularly preferred design, the invention is explained in more detail:

DETAILED DESCRIPTION OF THE INVENTION

Non-genetically treated *spirulina* powder (*Spirulina platensis* or *Arthrospira platensis*) was turned into pellets using a single-shaft extruder by Kahl, type OEE8.

The *Arthrospira* powder used exhibited the attributes listed in Table 1:

TABLE 1

| Parameter | Method/equipment | Measurement values |
|---|---|---|
| Colour | visual | dark green |
| Odour | DAB 10 (V.3.1.6) | characteristic |
| Consistency | visual | powder |
| Moisture | DAB 10 (V.6.22.N2) Absolute determinator at 105° C. | 3.92 g/100 g |
| Protein | § 35 LMBG L 17.00-15 Kjeldahl determinator | 54.75 g/100 g |
| Mineral substances | DAB 10 (V.3.2.16) Ashing | 5.65 g/100 g |
| Fat/lipids | Mod. according to § 35 LMBG L 17.00-4; extraction according to Weibull/Stoldt | 5.6 g/100 g |
| Algal toxins | HPLC, UV detection, mass spectrometer | cannot be detected |
| Chlorophyll | Jeffrey, S W and Humphrey, G F (1975) Biochem. Physiol. Pflanzen 167, 191-194, spectral photometer | 1.019 mg/100 g |

The total bacterial count was $7 \times 10^4$ bacteria/g of powder, the moiety of yeasts, moulds and coliform bacteria in each case being below 100 cells/g of powder (*escherichia coli* itself could not be detected).

The extruder used for this example is characterized by a high load capacity, the possibility to work at a high pressure (up to 150 bar), a high performance level (up to 11 kW), a hydraulically controlled die and the supply of liquids into the ongoing process. Using a touch panel, in particular pressure, speed of the extruder shaft, the addition of products and the supply of liquids, in this case water, can be controlled. Two temperature sensors enable monitoring and possible countermeasures by cooling. The extruder uses conical screws that can be adjusted in terms of the penetration depth and that replace the second shaft.

The particular advantage of the extrusion is the very short temperature loading of the microalgae powder of at most 2 minutes, as a function of the dwell time that has been set. As was found out, the co-operation of pressure and shear forces facilitates a high disruption rate despite a high disruption rate. In particular in the case of the extruder that is used it is possible to cool the extruder using a cooling liquid so that relatively low temperatures can be maintained across the entire process sequence.

In a first step, the *Arthrospira* powder is conveyed into the extruder using a metering screw. After a short kneading path, the powder is moistened by adding water in the range of in each case 2 L/h up to 4 L/h, inclusive. It is only now that mixing with water and shearing the *Arthrospira* powder/water mixture starts.

Preferably, the powder throughput during the entire process amounts to approximately 40 kg/h, the standard shaft (No. 3195-4456), that is preferably used, being operated at 300 rpm.

At the end of the screw, a die closes the extruder making it possible for the mixture of algae and water to exit the extruder only through holes and/or slots having a predetermined number and shape. Preferably a die having 14 holes having a hole diameter of in each case 3.0 mm is used. Necessarily, pressure and shear work together until the extrudate is pressed through the holes or slots. When the extrudate is discharged from the extruder through the die, evaporation of the solvent and the sudden temperature drop lead to an expansion of the extrudate.

A rotating blade head arranged behind the die preferably cuts the extrudate into pellets that dry and cool fast on account of the increased surface when falling down into a receptacle. Temperatures of up to 160° C. can be briefly occur at the die.

To extract the pharmaceutically effective *Arthrospira* ingredients, in each case 10 mL of ethyl acetate are added to 1 g of the extruded *Arthrospira* powder and incubated at 28° C. for 24 hours. After incubation, the solution is preferably filtered through a pleated filter and the solvent is evaporated in a rotary evaporator. Then the filtrate is preferably taken up in 1 mL of ethanol and filtered through a sterile filter.

Particularly preferably, the extract can be filtered further for decolouring and/or odour reduction, for example passed over an active-carbon column. The result is a clear solution having a specific odour.

The extract preferred according to the process that is preferably shown, exhibits a high degree of antimicrobial, in particular antibacterial and antifungal activity. The chitinase activity of the extract was measured as a measure for the bioactivity.

In an extract consisting of *Spirulina* Powder High Performance that was not extruded, but else treated as described above, a chitinase activity of 5.5 U/g could thus be detected.

In contrast, measuring the chitinase activity of the *Spirulina* Powder High Performance treated according to the inventive process using extrusion, exhibited an activity of 19.1 U/g, an increase of approximately 3.5 times relative to the untreated powder.

The effects of the algae extract against fungi, bacteria and viruses were carried out in vitro in the first step, i.e. classical Hemmhof test against fungi and bacteria. In particular bioactivity tests (i.a. Hemmhof tests) were carried out using *Propionibakterium acnes, Bacillus subtilis, Escherichia coli, Trichophytum rubrum, Trichophytum mentagrophytes* and herpes. The antiviral protective effect against herpes viruses (HHV-1) was tested on Vero cells. After successful positive in-vitro tests, further therapy surveys and case studies were carried out on patients to check the clinical effect.

The result shows an effect of the antimicrobial activity of the extract prepared according to the invention (extract 2), that is increased relative to the antimicrobial activity of an *Arthrospira* extract (extract 1) prepared without extruding the starting material. In addition, the measurement values (extract 1 and extract 2) obtained for *Arthrospira platensis* were compared to the antimicrobial activity of an extract from *Arthrospira maxima* (extract 3) prepared using the process according to the invention.

The test results listed in Table 2 show for *Propionibakterium acnes, Bacillus subtilis, Escherichia coli, Trichophytum rubrum, Trichophytum mentagrophytes* the bioactivity of the respective extract using the inhibiting effect of the extract in %. 0% designates all activities having an inhibiting effect of 30% and/or less. For herpes viruses, an inhibiting effect could be shown for extract solutions >2%.

TABLE 2

|  | P. acnes | B. subtilis | E. coli | T. rubrum | T. mentagrophytes |
| --- | --- | --- | --- | --- | --- |
| Extract 1-0.1% | 0 | 0 | 0 | 0 | 0 |
| Extract 1-1% | 98 | 33 | 0 | 43 | 40 |
| Extract 1-5% | 100 | 54 | 0 | 52 | 51 |
| Extract 2-0.1% | 0 | 0 | 0 | 0 | 0 |
| Extract 2-1% | 81 | 37 | 0 | 59 | 54 |
| Extract 2-5% | 100 | 56 | 45 | 73 | 65 |
| Extract 3-0.1% | 0 | 0 | 0 | 0 | 0 |
| Extract 3-1% | 87 | 35 | 0 | 51 | 45 |
| Extract 3-5% | 93 | 75 | 55 | 63 | 57 |

In a further experiment, the inhibition of further pathogens was studied when using 0.5% of the dissolved extract prepared according to the invention (Table 3):

TABLE 3

| Pathogen | Inhibition in percent |
| --- | --- |
| *Propionibacterium acnes* | 100% |
| *Staphylococcus epidermis* | 100% |
| *Staphylococcus aureus* | 100% |
| *Pseudomonas aeruginosa* | 90% |
| *Aspergillus niger* | 80% |
| *Dermabacter* | 90% |
| *Brevibacter* | 97% |
| *Trichoderma* types | 100% |

The inventive process enables the disruption of *Arthrospira* powder for preparing a pharmaceutically effective *Arthrospira* extract having increased antimicrobial activity. The process avoids complicated and expensive processes to increase the production of pharmaceutically active substances by the organism itself, but increases the yield of these substances in an extract of *Arthrospira cyanobacteria* that have been grown conventionally or also using physiological stress compared to extracts prepared using conventional processes.

The inventive extract is in particular suitable for use against diseases that are caused in particular by *Propionibacterium acnes, Staphylococcus epidermis, Staphylococcus aureus, Pseudomonas aeruginosa, Aspergillus niger, Dermabacter, Brevibacter* and *Trichoderma* types, individually or in combination. These diseases are in particular skin diseases, for example acne, herpes (in particular type I), blepharitis, endophtalmitis.

On top of this, case studies also showed an effect of the extract that has been prepared according to the invention, against viruses from the group of the human papillomaviruses (HPV).

The invention claimed is:

1. A process for preparing a pharmaceutically-effective *Arthrospira* extract having chitinase activity comprising the steps of:
    extruding a mixture of water and a powder containing an effective amount of an *Arthrospira* sp. to form an extrudate; and
    extracting the extrudate with an organic solvent to obtain said *Arthrospira* extract.

2. The process according to claim 1, wherein the extruding takes place at a temperature of between 130° C. and 160° C. and a pressure of between 8 MPa and 13 MPa.

3. The process according to claim 1, wherein the organic solvent is ethyl acetate.

4. The process according to claim 1, wherein the extracting takes place at 28° C. for 24 h.

5. The process according to claim 1, further comprising the following steps after the extracting step:
    removing the solvent; and
    filtration of the extract to discolor or deodorize the extract, to obtain a filtered extract.

6. The process according to claim 5, wherein the filtered extract is further taken up in ethanol and/or is filtered through a sterile filter.

7. The process according to claim 1, wherein during extruding between 2 L and 4 L of water is added per hour to the powder at a throughput of 40 kg of powder per hour.

8. The process according to claim 1, wherein the extracting takes place using 10 mL of organic solvent per 1 g of extrudate and wherein the organic solvent is ethyl acetate.

9. The process according to claim 1, wherein the cyanobacterium is *Arthrospira maxima, Arthrospira fusiformis* or *Arthrospira platensis*.

10. The process according to claim 2, wherein the organic solvent is ethyl acetate.

11. The process according to claim 2, wherein the extruding takes place at 28° C. for 24 h.

12. The process according to claim 2, further comprising the following steps after the extracting step:
    removing the solvent;
    filtration of the extract to discolor or deodorize the extract to obtain a filtered extract.

13. The process according to claim 3, further comprising the following steps after the extracting step:
    removing the solvent;
    filtration of the extract to discolor or deodorize the extract to obtain a filtered extract.

14. The process according to claim 2, characterized in that the *Arthrospira* sp. is *Arthrospira maxima, Arthrospira fusiformis* or *Arthrospira platensis*.

15. The process according to claim 1, characterized in that the *Arthrospira* sp. is *Arthrospira maxima, Arthrospira fusiformis* or *Arthrospira platensis*.

16. The process according to claim 1, wherein the extract has a chitinase activity of about 3.5 times greater than an unprocessed powder containing the *Arthrospira* sp.

17. The process according to claim 16, wherein the extract has a chitinase activity of about 19.1 U/g.

* * * * *